United States Patent [19]

De Vos et al.

[11] Patent Number: 5,393,799

[45] Date of Patent: Feb. 28, 1995

[54] PROCESS FOR RIGID FOAMS

[75] Inventors: Rik De Vos, Rotselaar; David Thorpe, Erps-Kwerps; Gonda Van Essche, Leuven, all of Belgium

[73] Assignee: Imperial Chemical Industries PLC, London, England

[21] Appl. No.: 163,459

[22] Filed: Dec. 6, 1993

[30] Foreign Application Priority Data

| Dec. 30, 1992 | [GB] | United Kingdom | 9227105 |
| Dec. 30, 1992 | [GB] | United Kingdom | 9227106 |
| Mar. 24, 1993 | [GB] | United Kingdom | 9306065 |
| Mar. 24, 1993 | [GB] | United Kingdom | 9306066 |

[51] Int. Cl.$^6$ ............................................ C08G 18/00
[52] U.S. Cl. .................................. 521/157; 521/159
[58] Field of Search ........................... 521/157, 159

[56] References Cited

U.S. PATENT DOCUMENTS

| 3,575,899 | 4/1971 | Pryor | 260/17.4 |
| 3,746,689 | 7/1973 | Narayan et al. | 260/77.5 |
| 3,891,579 | 6/1975 | Cenker et al. | 260/2.5 |
| 4,540,765 | 9/1985 | Koemm et al. | 528/45 |
| 4,792,354 | 12/1988 | Matsuo et al. | 106/2 |
| 4,835,300 | 5/1989 | Fukui et al. | 560/25 |
| 4,972,002 | 11/1990 | Volkert | 521/120 |
| 4,981,879 | 1/1991 | Snider | 521/131 |
| 5,034,424 | 7/1991 | Wenning et al. | 521/109 |
| 5,171,877 | 12/1992 | Knaup et al. | 562/26 |
| 5,200,493 | 4/1993 | Jacobson et al. | 528/70 |
| 5,204,441 | 4/1993 | Baum et al. | 528/70 |
| 5,214,121 | 5/1993 | Mosch et al. | 528/49 |
| 5,254,660 | 10/1993 | Kirchmeyer et al. | 528/49 |

FOREIGN PATENT DOCUMENTS

| 734497 | 5/1966 | Canada . |
| 0273449 | 7/1988 | European Pat. Off. . |
| 0283892 | 9/1988 | European Pat. Off. . |
| 0298364 | 1/1989 | European Pat. Off. . |
| 0322759 | 7/1989 | European Pat. Off. . |
| 0325918 | 8/1989 | European Pat. Off. . |
| 0508649 | 10/1992 | European Pat. Off. . |
| 1794356 | 2/1973 | Germany . |
| 2415150 | 10/1975 | Germany . |
| 04146917 | of 0000 | Japan . |
| 6163646 | of 0000 | Japan . |
| 62045786 | of 0000 | Japan . |
| 62205181 | of 0000 | Japan . |
| 92/17635 | 10/1992 | WIPO . |

*Primary Examiner*—Maurice J. Welsh

[57] ABSTRACT

Process for the preparation of rigid polyurethane foam by reaction of a polyfunctional isocyanate-reactive composition with a polyisocyanate composition comprising the reaction product of a stoichiometric excess of an organic polyisocyanate and a substantially fluorinated isocyanate-reactive compound, optionally in the presence of an inert, insoluble fluorinated compound.

23 Claims, No Drawings

PROCESS FOR RIGID FOAMS

This invention relates to processes for the preparation of rigid polyurethane or urethane-modified polyisocyanurate foams, to foams prepared thereby, and to certain novel polyisocyanate compositions useful in the process.

Rigid polarethane and urethane-modified polyisocyanurate foams are in general prepared by reacting the appropriate polyisocyanate and polyol in the presence of a blowing agent. One use of such foams is as a thermal insulation medium as for example in the construction of refrigerated storage devices. The thermal insulating properties of rigid foams are dependent upon a number of factors including, for closed cell rigid foams, the cell size and the thermal conductivity of the contents of the cells.

A class of materials which has been widely used as blowing agent in the production of polyurethane and urethane-modified polyisocyanurate foams is the fully halogenated chlorofluorocarbons, and in particular trichlorofluoromethane (CFC-11). The exceptionally low thermal conductivity of these blowing agents, and in particular of CFC-11, has enabled the preparation of rigid foams having very effective insulation properties. Recent concern over the potential of chlorofluorocarbons to cause depletion of ozone in the atmosphere has led to an urgent need to develop reaction systems in which chlorofluorocarbon blowing agents are replaced by alternative materials which are environmentally acceptable and which also produce foams having the necessary properties for the many applications in which they are used.

The present Applicant has now developed an improved process for the preparation of rigid polyurethane and urethane-modified polyisocyanurate foams derived from certain fluorinated polyisocyanate compositions.

Processes for the preparation of polyurethane materials derived from fluorinated polyisocyanate compositions have been reported, for example in German patent applications nos 2415150 and 1794356, in European patent application nos 283892 and 322759, in Japanese patent applications Kokai nos 61/63646, 62/45786 and 62/205181 and in U.S. Pat. Nos. 5,171,877, 3,575,899, 4,540,765 and 4,835,300. The obtained polyurethane materials are described for textile treatment to impart i.a. oil—and water—repellent properties or for use as coatings. In Canadian patent no. 734497 is described the use of a fluorine containing Urethane as surface active agent i.a. in the manufacture of polyurethane foams. Processes for the preparation of polyurethane materials derived from fluorinated polyisocyanate compositions under foam-forming conditions have not been reported.

Accordingly the invention provides a process for the preparation of a rigid polyurethane or urethane-modified polyisocyanurate foam by reaction of a polyisocyanate composition with a polyfunctional isocyanate-reactive composition under foam-forming conditions, characterized in that the polyisocyanate composition comprises the reaction product of a stoichiometric excess of an organic polyisocyanate and (a) substantially fluorinated isocyanate-reactive compound(s).

Rigid polyurethane and urethane-modified polyisocyanurate foams prepared by the process of the invention are characterized by having a fine cell structure and excellent thermal insulation properties with no degradation of mechanical properties, and the process of the invention is therefore particularly suitable for the preparation of rigid foams for thermal insulation applications in the presence of alternative blowing agents. Furthermore, the substantially fluorinated, isocyanate-reactive compounds from which the polyisocyanate compositions used in the process of the invention are derived and which, it is believed, are responsible for the improved thermal insulation properties of the resulting foams, become fully incorporated into the chemical structure of the foam, and are not, therefore, released into the environment either during or after the foam-forming process.

The term 'substantially fluorinated isocyanate-reactive compound' as used herein is to be understood to refer to any organic compound having at least one isocyanate-reactive functional group in which at least 50% of those hydrogen atoms bonded to carbon atoms in the corresponding unfluorinated compound are replaced by fluorine atoms.

Suitable substantially fluorinated isocyanate-reactive compounds for use in the process of the invention are those of formula (I):

[H—Y—(CH$_2$)$_m$—(Z')$_{q'}$]$_p$—A—(Z)$_q$—(CH$_2$)$_n$—X—H     (I)

wherein n is an integer of from 1 to 11;
m is 1 to 11;
p is 0 or 1;
q is 0 or 1;
q' is 0 or 1;
Y is oxygen, sulphur, the group of formula

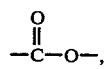

or a group of formula

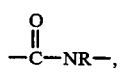

—SO$_2$—NR— or —NR—, where R is hydrogen, C$_{1-12}$ alkyl, or C$_{1-12}$ fluorinated alkyl;
X is oxygen, sulphur, the group of formula

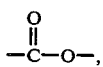

or a group of formula

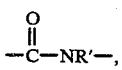

—SO$_2$—NR'— or —NR'—, where R' is C$_{1-12}$ alkyl, C$_1$ fluorinated alkyl, hydrogen or the group of formula —(CH$_2$)$_n$—(Z)$_q$—A—[(Z')$_{q'}$—(CH$_2$)$_m$—Y—H]$_p$;
Z and Z' each independently are groups of formula

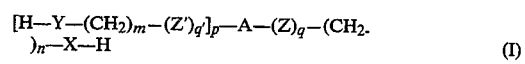

or —SO$_2$—NR'' where R'' is hydrogen, C$_{1-12}$ alkyl, C$_{1-12}$ fluorinated alkyl or the group of formula —CH$_2$-

$)_n$—A—[(CH$_2$)$_m$—Y—H]$_p$ or the group of formula —R'''—Y—H where R''' is C$_{1-12}$ alkylene; and either (i) when p is 0, A is a substantially fluorinated or perfluorinated straight or branched chain alkyl group containing from 2 to 10 carbon atoms; or (ii) when p is 1, A is a substantially fluorinated or perfluorinated, straight or branched chain alkylene group containing from 2 to 10 carbon atoms.

One group of preferred substantially fluorinated isocyanate-reactive compounds for use in the process of the invention are those of formula (I) as defined above wherein X and Y are both oxygen, and A, Z, Z', n, m, p, q and q' have any of the meanings given above. Preferably p is 0.

Particularly preferred substantially fluorinated isocyanate-reactive compounds for use in the process of the invention are those of formula (II)

A—(CH$_2$)$_n$—OH     (II)

wherein A is a substantially fluorinated or perfluorinated, straight or branched chain alkyl group containing from 2 to 10 carbon atoms and n is 1 to 11. Particular mention may be made of those compounds of Formula (II) wherein n is 1 or 2 and A is perfluorinated C$_{3-10}$, straight or branched chain alkyl, such as (perfluoropropyl)methanol, (perfluorobutyl)methanol, (perfluoropentyl)methanol, (perfluorohexyl)methanol, (perfluoroheptyl)methanol, (perfluorooctyl)methanol, (perfluorononyl)methanol, (perfluoroethyl)ethanol, (perfluoropropyl)ethanol, (perfluorobutyl)ethanol, (perfluoropentyl)ethanol, (perfluorohexyl)ethanol, (perfluoroheptyl)ethanol and (perfluorooctyl)ethanol.

Another particularly preferred group of substantially fluorinated isocyanate-reactive compounds for use in the process of the invention are those of formula (III)

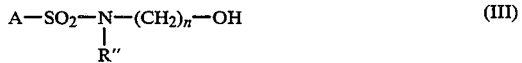

A—SO$_2$—N—(CH$_2$)$_n$—OH     (III)
         |
         R"

wherein A is a substantially fluorinated or perfluorinated, straight or branched chain alkyl group containing from 2 to 10 carbon atoms, n is 1 to 11 and R" is hydrogen or a C$_{1-12}$ alkyl or R''' —OH wherein R''' is C$_{1-12}$ alkylene. Particular mention may be made of those compounds of formula (III) wherein n is 1 or 2 and A is perfluorinated C$_{6-8}$ straight or branched chain alkyl and R" is hydrogen or C$_{1-4}$ alkyl or R''' OH wherein R''' is C$_{1-4}$ alkylene such as N-ethyl-N-2-hydroxyethylperfluorooctane sulfonamide, N-methyl-N-2-hydroxyethylperfluorooctane sulfonamide, N-propyl-N-2-hydroxyethylperfluorooctane sulfonamide, N-2-hydroxyethylperfluorooctane sulfonamide, N-ethyl-N-2-hydroxymethylperfluorooctane sulfonamide, N-methyl-N-2-hydroxymethyl-perfluorooctane sulfonamide, N-propyl-N-2-hydroxymethylperfluorooctane sulfonamide, N-2-hydroxymethylperfluorooctane sulfonamide, N-methyl-N-2-hydroxyethylperfluorohexane sulfonamide and bis-N-2-hydroxyethylperfluorooctane sulfonamide.

Suitable organic polyisocyanates with which the substantially fluorinated isocyanate-reactive compound(s) may be reacted to form the polyisocyanate composition for use in the process of the invention include any of those known in the art for the preparation of rigid polyurethane or urethane-modified polyisocyanurate foams, and in particular the aromatic polyisocyanates such as diphenylmethane diisocyanate in the form of its 2,4'-, 2,2'- and 4,4'-isomers and mixtures thereof, the mixtures of diphenylmethane diisocyanates (MDI) and oligomers thereof known in the art as "crude" or polymeric MDI (polymethylene polyphenylene polyisocyanates) having an isocyanate functionality of greater than 2, toluene diisocyanate in the form of its 2,4- and 2,6-isomers and mixtures thereof, 1,5-naphthalene diisocyanate and 1,4-diisocyanatobenzene. Other organic polyisocyanates which may be mentioned include the aliphatic diisocyanates such as isophorone diisocyanate, 1,6-diisocyanatohexane and 4,4'-diisocyanatodicyclohexylmethane.

The polyisocyanate compositions used in the process of the invention may be conveniently prepared by addition of a particular substantially fluorinated isocyanate-reactive compound to the organic polyisocyanate or by addition of a mixture of several different substantially fluorinated isocyanate-reactive compounds to the organic polyisocyanate, for example under the conditions well known in the art for the preparation of isocyanate-ended prepolymers. Suitably, the addition is performed at an elevated temperature in the range from 50° C. to 100° C. with thorough mixing of the components, and mixing continued at the elevated temperature until substantially all of the isocyanate-reactive compound has reacted with the organic polyisocyanate. Preferably the substantially fluorinated isocyanate-reactive compound(s) is (are) added in an amount in the range from 0.02 to 5.0% preferably 0.1 to 3.0% by weight based on the weight of organic polyisocyanate.

In order to improve the stability of the polyisocyanate compositions used in the process of the present invention, it is advantageous to use the allophanate variant of the obtained fluorinated isocyanate-ended prepolymer. This allophanate variant can be prepared by reaction of the obtained fluorinated isocyanate-ended prepolymer with the organic polyisocyanate itself in the presence of a suitable catalyst. Another method for improving the stability of the polyisocyanate compositions used in the process of the present invention is to use so-called mixed prepolymers obtained by reaction of organic polyisocyanate with a mixture of two or more different substantially fluorinated isocyanate-reactive compounds. Allophanate variants of these mixed prepolymers can also be used. Examples of such preferred mixed prepolymers include prepolymers derived from N-ethyl, N-2-hydroxyethylperfluorooctane sulfonamide and N-methyl-N-2-hydroxyethyl perfluorooctane sulfonamide in ratios varying from 10:1 to 1:10 and preferably from 5:5 to 1:9, prepolymers derived from (perfluorohexyl)(m)ethanol and N-ethyl- or N-methyl-N-2-hydroxyethylperfluorooctane sulfonamide in ratios varying from 10:1 to 1:10, preferably about 1:1.

The polyisocyanate composition for use in the process of the present invention may comprise only one type of said reaction product or may comprise different types of said reaction product derived from different substantially fluorinated isocyanate-reactive compounds and/or different polyisocyanates. polyfunctional isocyanate-reactive compositions with which the polyisocyanate composition may be reacted to form rigid polyurethane or urethane-modified polyisocyanurate foams include any of those known in the art for that purpose. Of particular importance for the preparation of rigid foams are polyols and polyol mixtures having average hydroxyl numbers of from 300 to 1000, especially from 300 to 700 mg KOH/g, and hydroxyl functionalities of from 2 to 8, especially from 3 to 8. Suitable polyols have been fully described in the prior art and include reaction products of alkylene oxides, for example ethylene oxide and/or propylene oxide, with initiators containing from 2 to 8 active hydrogen atoms per molecule. Suitable initiators include: polyols, for example glycerol, trimethylolpropane, triethanolamine, pentaerythritol, sorbitol and sucrose; polyamines, for example ethylene diamine, tolylene diamine, diaminodiphenylmethane and polymethylene polyphenylene polyamines; and aminoalcohols, for example ethanolamine and diethanolamine, and mixtures of such initiators. Other suitable polymeric polyols include polyesters obtained by the condensation of appropriate proportions of glycols and higher functionality polyols with dicarboxylic or polycarboxylic acids. Still further suitable polymeric polyols include hydroxyl terminated polythioethers, polyamides, polyesteramides, polycarbonates, polyacetals, polyolefins and polysiloxanes. The quantities of the polyisocyanate compositions and the polyfunctional isocyanate-reactive compositions to be reacted will depend upon the nature of the rigid polyurethane or urethane-modified polyisocyanurate foam to be produced and will be readily determined by those skilled in the art.

The process of the invention is carried out in the presence of any of the blowing agents known in the art for the preparation of rigid polyurethane or urethane-modified polyisocyanurate foams. Such blowing agents include water or other carbon dioxide-evolving compounds, or inert low boiling compounds having a boiling point of above $-70°$ C. at atmospheric pressure.

Where water is used as blowing agent, the amount may be selected in known manner to provide foams of the desired density, typical amounts being in the range from 0.05 to 5% by weight based on the total reaction system.

Suitable inert blowing agents include those well known and described in the art, for example hydrocarbons, dialkyl ethers, alkyl alkanoates, aliphatic and cycloaliphatic hydrofluorocarbons, hydrochlorofluorocarbons, chlorofluorocarbons, hydrochlorocarbons and fluorine-containing ethers.

Preferred blowing agents for use in the process of the present invention are those having boiling points between $-70°$ C. and $+80°$ C. at atmospheric pressure. In view of the improved thermal insulation properties associated with foams prepared by the process of the invention, the use of fully halogenated chlorofluorocarbon blowing agents may advantageously be avoided.

Examples of preferred blowing agents include pentane, cyclopentane, isopentane and dichlorofluoroethane.

The total quantity of blowing agent to be used in a reaction system for producing cellular polymeric materials will be readily determined by those skilled in the art, but will typically be from 2 to 25% by weight based on the total reaction system.

In addition to the polyisocyanate and polyfunctional isocyanate-reactive compositions and the blowing agent, the foam-forming reaction mixture will commonly contain one or more other auxiliaries or additives conventional to formulations for the production of rigid polyurethane and urethane-modified polyisocyanurate foams. Such optional additives include crosslinking agents, for example low molecular weight polyols such as triethanolamine, foam-stabilizing agents or surfactants, for example siloxane-oxyalkylene copolymers, urethane catalysts, for example tin compounds such as stannous octoate or dibutyltin dilaurate or tertiary amines such as dimethylcyclohexylamine or triethylene diamine, and fire retardants, for example halogenated alkyl phosphates such as trig chloropropyl phosphate.

In a further aspect of the invention, it has been found that even greater improvements in thermal insulation properties and cell size may be achieved using the process of the invention if an inert, insoluble fluorinated compound is additionally incorporated into the foam-forming reaction mixture. The invention additionally provides, therefore, a process for the preparation of a rigid polyurethane or urethane-modified polyisocyanurate foam by reaction of a polyisocyanate composition with a polyfunctional isocyanate-reactive composition, in the presence of an inert, insoluble fluorinated compound and under foam-forming conditions, characterized in that the polyisocyanate composition comprises the reaction product of a stoichiometric excess of an organic polyisocyanate and (a) substantially fluorinated isocyanate-reactive compound(s).

The term inert as used herein with reference to the inert, insoluble fluorinated compound used in the process of the invention is to be understood as indicating a substantial lack of chemical reactivity with any of the other components used in the foam-forming reaction.

The term insoluble as used herein with reference to the inert, insoluble fluorinated compound used in the process of the invention is defined as showing a solubility in either the isocyanate-reactive composition or the polyisocyanate composition with which it is to be blended of less than 500 ppm by weight at 25° C. and atmospheric pressure.

Inert, insoluble fluorinated compounds for use in the process of the invention include any of those disclosed in U.S. Pat. No. 4,981,879, U.S. Pat. No. 5,034,424, U.S. Pat. No. 4,792,002, European Patent Application No 0508649 and No 0498628. It is preferred, however, to use an inert, insoluble, substantially fluorinated or perfluorinated compound having a boiling point of at least 20° C. at atmospheric pressure, and preferably at least 40° C. and more preferably at least 60° C., or 80° C. or 100° C. Suitable compounds include substantially fluorinated or perfluorinated hydrocarbons, substantially fluorinated or perfluorinated ethers, substantially fluorinated or perfluorinated tertiary amines, substantially fluorinated or perfluorinated amino-ethers and substantially fluorinated or perfluorinated sulphones.

The terms substantially fluorinated or perfluorinated as used herein with reference to the inert, insoluble fluorinated compound used in the process of the invention are to be understood to embrace compounds in which at least 50% of the hydrogen atoms of the unfluorinated compounds are replaced by fluorine.

Examples of preferred inert, insoluble fluorinated compounds for use in the process of the present invention include perfluoro-n-pentane, perfluoro-n-hexane, perfluorinated alkyltetrahydrofurans such as perfluorinated butyltetrahydrofuran and perfluorinated N—($C_{1-6}$ alkyl)-morpholines.

The inert, insoluble fluorinated compound is used in amounts ranging from 0.01 to 5% by weight based on the total foam-forming reaction mixture.

The inert, insoluble fluorinated compound is added to the polyisocyanate composition or to the isocyanate-reactive composition or to both compositions.

Certain inert, insoluble fluorinated compounds suitable for use in the process of the invention may themselves act as blowing agents under the conditions pertaining to the foam-forming reaction, particularly where their boiling point is lower than the exotherm temperature achieved by the reaction mixture. For the avoidance of doubt, such materials may, partly or completely, fulfill the function of blowing agent in addition to that of inert, insoluble fluorinated compound.

In operating the process for making rigid foams according to the invention, the known one-shot, prepolymer or semi-prepolymer techniques may be used together with conventional mixing methods and the rigid foam may be produced in the form of slabstock, mouldings, cavity fillings, sprayed foam, frothed foam or laminates with other materials such as hardboard, plasterboard, plastics, paper or metals.

The process of the present invention is suitable not only for making closed celled rigid polyurethane foam but also for making open celled rigid polyurethane foam with the same effect of reducing cell size and improving thermal insulation. In particular, open celled rigid polyurethane foams can be prepared according to the method described in European patent application no. 0498628 using the present polyisocyanate composition comprising the reaction product of a stoichiometric excess of an organic polyisocyanate and (a) substantially fluorinated isocyanate-reactive compound(s). This method involves reacting a polyisocyanate composition with a polyfunctional isocyanate-reactive composition in the presence of an isocyanate-reactive cyclic carbonate (such as glycerol carbonate) or isocyanate-reactive cyclic urea (such as Fixapret NF available from BASF) as blowing promotor and in the presence of an inert, insoluble fluorinated compound and in the presence of a metal salt catalyst. The polyisocyanate composition may comprise besides the present reaction product of a stoichiometric excess of an organic polyisocyanate and (a) substantially fluorinated isocyanate-reactive compound(s), a composition as described in European patent application no. 543536 comprising a urethane-modified isocyanate-ended prepolymer.

This latter composition may advantageously be added as a third stream. The ratio between the present reaction product and this latter composition is preferably between 70:30 and 80:20.

Certain of the polyisocyanate compositions useful in the process of the invention have not been previously described. In a further aspect, therefore, the invention provides a polyisocyanate composition comprising the reaction product of a stoichiometric excess of an organic polyisocyanate and (a) substantially fluorinated isocyanate-reactive compound(s) characterized in that the organic polyisocyanate is diphenylmethane diisocyanate in the form of its 2,4'-, 2,2'- or 4,4'-isomer, or an oligomeric polymethylene polyphenylene polyisocyanate, or any mixture thereof, and the substantially fluorinated isocyanate-reactive compound is a compound of formula (I):

$$[H-Y-(CH_2)_m-(Z')_{q'}]_p-A-(Z)_q-(CH_2)_n-X-H \quad (I)$$

wherein n is 1 an integer of from 1 to 11;
m is 1 to 11;
p is 0 or 1;
q is 0 or 1;
q' is 0 or 1;
Y is oxygen, sulphur, the group of formula

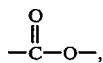

or a group of formula

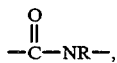

—$SO_2$—NR— or —NR—, where R is hydrogen, $C_{1-12}$ alkyl, or $C_{1-12}$ fluorinated alkyl;
X is oxygen, sulphur, the group of formula

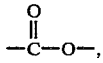

or a group of formula

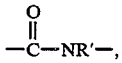

—$SO_2$—NR'— or —NR'—, where R' is $C_{1-12}$ alkyl, $C_{1-12}$ fluorinated alkyl, hydrogen or the group of formula —$(CH_2)_n$—$(Z)_q$—A—$[(Z')_{q'}$—$(CH_2)_m$—Y—H$]_p$;
Z and Z' each independently are groups of formula

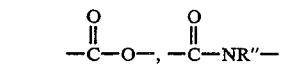

or —$SO_2$— NR'' where R'' is hydrogen, $C_{1-12}$ alkyl, $C_{1-12}$ fluorinated alkyl or the group of formula —$(CH_2)_n$—A—$[(CH_2)_m$—Y—H$]_p$ or the group of formula —R'''—Y—H where R''' is $C_{1-12}$ alkylene;
and either
(i) when p is 0, A is a substantially fluorinated or perfluorinated, straight or branched chain alkyl group containing from 2 to 10 carbon atoms;
or
(ii) when p is 1, A is substantially fluorinated or perfluorinated, straight or branched chain alkylene group containing from 2 to 10 carbon atoms.

Particularly preferred novel polyisocyanate compositions provided by the invention are those wherein the substantially fluorinated isocyanate-reactive compound is a compound of formula (II)

$$A-(CH_2)_n-OH \quad (II)$$

wherein A is a substantially fluorinated or perfluorinated, straight or branched chain alkyl group containing from 2 to 10 carbon atoms and n is 1 to 11.

Particular mention may be made of those novel polyisocyanate compositions provided by the invention wherein the substantially fluorinated isocyanate-reactive compound is a compound of Formula (II) wherein n is 1 or 2 and A is perfluorinated $C_{3-10}$, straight or branched chain alkyl.

Other particularly preferred novel polyisocyanate compositions provided by the invention are those wherein the substantially fluorinated isocyanate-reactive compound is a compound of formula (III)

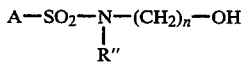

wherein A is a substantially fluorinated or perfluorinated, straight or branched chain alkyl group containing from 2 to 10 carbon atoms, n is 1 to 11 and R" is hydrogen or a $C_{1-12}$ alkyl or R"' —OH wherein R"' is $C_{1-12}$ alkylene.

Particular mention may be made of those compounds of formula (III) wherein n is 1 or 2 and A is perfluorinated $C_{6-8}$ straight or branched chain alkyl and R" is hydrogen or $C_{1-4}$ alkyl or R"' —OH wherein R"' is $C_{1-4}$ alkylene.

According to a preferred embodiment of the present invention the novel polyisocyanate composition comprises the reaction product of a stoichiometric excess of the organic polyisocyanate and two or more different substantially fluorinated isocyanate-reactive compounds.

According to another preferred embodiment of the present invention the novel polyisocyanate composition comprises the allophanate variant of said reaction product.

In a preferred aspect, the novel polyisocyanate composition provided by the invention comprise the reaction product of an organic polyisocyanate as hereinbefore described and from 0.02 to 5.0% preferably 0.1 to 3.0% by weight, based on the weight of the organic polyisocyanate, of (a) substantially fluorinated isocyanate-reactive compound(s) as hereinbefore described.

In a further preferred aspect of the present invention the novel polyisocyanate compositions comprising the reaction product as specified hereinbefore further comprise an inert, insoluble fluorinated compound as described hereinbefore. The inert, insoluble fluorinated compound is used in amounts ranging from 0.1 to 10% by weight, preferably from 1 to 5% by weight based on the total polyisocyanate composition. In order to stabilize the obtained emulsion a non-isocyanate-reactive surfactant may be added such as Tegostab B 8407, a silicone based surfactant available from Goldschmidt and SR 234 available from Union Carbide.

The various aspects of this invention are illustrated, but not limited by the following examples in which the following materials are referred to:

Polyol A
An oxypropylated sugar of hydroxy value 400 mg KOH/g
Suprasec DNR
Polymeric MDI having an NCO content of 30.7% (from Imperial Chemical Industries PLC)
Catalyst SFC
A tertiary amine catalyst from Imperial Chemical Industries PLC.
Niax A1
A tertiary amine catalyst from Union Carbide
DC 193
A silicon based surfactant from DOW Corning.
FC75
A perfluorinated liquid having a boiling point of 102° C. available from 3M.
FC430
A fluorinated surfactant from 3M.
HCFC-141b
Dichlorofluoroethane (blowing agent)
Polyol B
A polyether polyol derived from diamino diphenylmethane of hydroxy value 500 mg KOH/g
Catalyst SFB
A tertiary amine catalyst from Imperial Chemical Industries PLC
Rubinate M
Polymeric MDI from Imperial Chemical Industries.
Fluowed EA800
A perfluoroalcohol from Hoechst.
L 4528
A perfluoroalcohol from 3M.
Daltolac XR 159
A polyether polyol from Imperial Chemical Industries.
Daltolac XR 144
A polyether polyol from Imperial Chemical Industries.
Daltolac R170
A polyether polyol from Imperial Chemical Industries.
Daltocel F455
A polyether polyol from Imperial Chemical Industries.
Arconate 1000
Propylene carbonate from ARCO.
RS 201
A surfactant from Union Carbide.
Polycat 5
A catalyst from Air Products.
Polyol C
A polyether polyol having a functionality of 2, a OH value of 54 and a molecular weight of 2200.
Catalyst LB
A metal salt catalyst from Imperial Chemical Industries.
Fixapret NF
A cyclic urea from BASF.
B8407
A surfactant from Goldschmidt.
Suprasec 2021
A polyisocyanate from Imperial Chemical Industries.

EXAMPLE 1

A polyisocyanate composition was prepared by the addition under intense stirring of 0.25 part by weight of (perfluoro-n-heptyl)methanol [formula $CF_3(CF_2)_6CH_2OH$] to 100 parts by weight of Suprasec DNR at a temperature of 80° C. The reaction mixture was stirred at 80° C. for a total of three hours to ensure complete reaction of the isocyanate-reactive material. The resulting polyisocyanate composition (referred to hereinafter as Polyisocyanate 1A) exhibited an isocyanate value of 30.3 and was used for the preparation of a rigid polyurethane foam according to Example 2.

EXAMPLE 2

Rigid polyurethane foams were prepared by standard procedures by reaction of a polyol with Polyisocyanate 1A (prepared according to the method of Example 1) and with unmodified Suprasec DNR for comparative purposes. The processes were repeated in the presence of an inert, insoluble fluorinated compound. The formulations used for foam preparation (components expressed in parts by weight—pbw) and various properties of the resultant foams are recorded in Table 1. The results indicate a significant improvement in cell size and initial thermal conductivity (lambda) for a foam prepared according to the process of the invention when compared to the corresponding foam prepared using a standard, unmodified polyisocyanate composition, and an even greater improvement when the process of the invention is carried out in the presence of an inert, insoluble fluorinated compound.

TABLE 2

| REACTION COMPONENTS | | | | | | | | | |
|---|---|---|---|---|---|---|---|---|---|
| POLYOL B | pbw | 100 | 100 | 100 | 100 | 100 | 100 | 100 | 100 |
| Catalyst SFB | pbw | 3 | 3 | 3 | 3 | 3 | 3 | 3 | 3 |
| Catalyst SFC | pbw | 1.8 | 1.8 | 1.8 | 1.8 | 1.8 | 1.8 | 1.8 | 1.8 |
| Niax A1 | pbw | 0.1 | 0.1 | 0.1 | 0.1 | 0.1 | 0.1 | 0.1 | 0.1 |
| DC 193 | pbw | 4 | 4 | 4 | 4 | 4 | 4 | 4 | 4 |
| $H_2O$ | pbw | 1.5 | 1.5 | 1.5 | 1.5 | 1.5 | 1.5 | 1.5 | 1.5 |
| HCFC 141b | pbw | 39 | 39 | 39 | 39 | — | — | — | — |
| Cyclopentane | pbw | — | — | — | — | 23.3 | 23.3 | 23.3 | 23.3 |
| FC 430 | pbw | — | 4 | — | 4 | — | 4 | — | 4 |
| FC 75 | pbw | — | — | 8.7 | 8.7 | — | — | 8.7 | 8.7 |
| Suprasec DNR | pbw | 152.8 | 152.8 | — | — | 152.8 | 152.8 | — | — |
| Polyisocyanates 1B | pbw | — | — | 154.8 | 154.8 | — | — | 154.8 | 154.8 |
| FOAM PROPERTIES | | | | | | | | | |
| DENSITY | kg/m³ | 28.6 | 28.8 | 29.2 | 29.1 | 29.4 | 28.6 | 30.1 | 28.5 |
| LAMDA INITIAL | mW/m°K | 18.3 | 18.4 | 17.8 | 17.7 | 20.4 | 19.7 | 19.6 | 19 | tion, and an even greater improvement when the process of the invention is carried out in the presence of an inert, insoluble fluorinated compound.

TABLE 1

| REACTION COMPONENTS | | | | | |
|---|---|---|---|---|---|
| POLYOL A | pbw | 100 | 100 | 100 | 100 |
| SFC | pbw | 2.5 | 2.5 | 2.5 | 2.5 |
| NIAX A1 | pbw | 0.2 | 0.2 | 0.2 | 0.2 |
| DC 193 | pbw | 4 | 4 | 4 | 4 |
| WATER | pbw | 0.8 | 0.8 | 0.8 | 0.8 |
| HCFC 141b | pbw | 21.8 | 21.8 | 21.8 | 21.8 |
| FC75 | pbw | — | — | 2 | 2 |
| FC 430 | pbw | — | — | 2 | 2 |
| SUPRASEC DNR | pbw | 141.6 | — | 141.6 | — |
| POLYISOCYANATE 1A | pbw | — | 142.6 | — | 142.6 |
| FOAM PROPERTIES | | | | | |
| DENSITY | kg/m³ | 34.3 | 33.8 | 32.7 | 33.1 |
| CELL SIZE | mm | 0.35 | 0.25 | 0.19 | 0.15 |
| LAMBDA INITIAL | mW/m°K at 10° C. | 18.5 | 17.5 | 17.3 | 16.6 |

EXAMPLE 3

A polyisocyanate composition was prepared by the addition under intense stirring of 1 part by weight of Fluorad FC 10 supplied by 3M (Fluorad is a trademark of 3M) (formula $C_nF_{2n+1}SO_2N(C_2H_5)C_2H_4OH$ with n approximately 7.5) to 100 parts by weight of Suprasec DNR at a temperature of 80° C. The reaction mixture was stirred at 80° C. for a total of three hours to ensure complete reaction of the isocyanate-reactive material. The resulting polyisocyanate composition (referred to hereinafter as Polyisocyanate 1B) was used for the preparation of a rigid polyurethane foam according to Example 4.

EXAMPLE 4

Rigid polyurethane foams were prepared by standard procedures by reaction of a polyol with polyisocyanate 1B (prepared according to the method of Example 3) and with unmodified Suprasec DNR for comparative purposes. The processes were repeated in the presence of an inert, insoluble fluorinated compound. The formulations used for foam preparation (components expressed in parts by weight—pbw) and various properties of the resultant foams are recorded in Table 2. The results indicate a significant improvement in initial thermal conductivity (lambda) for a foam prepared according to the process of the invention when compared to the corresponding foam prepared using a standard, unmodified polyisocyanate composition, and an even greater improvement when the process of the invention is carried out in the presence of an inert, insoluble fluorinated compound.

EXAMPLE 5

A polyisocyanate composition was prepared by the addition under intense stirring of 1 part by weight of Fluowed EA 800 (formula $C_6F_{13}$—$(CH_2)_2OH$) to 100 parts by weight of Rubinate M at a temperature of 84° C. under a nitrogen blanket. The reaction mixture was stirred at 84° C. for a further 2 hours. The resulting polyisocyanate composition is referred to hereinafter as Polyisocyanate 2A.

Another polyisocyanate composition (referred to hereinafter as Polyisocyanate 2B) was prepared by adding under intense stirring 0.06 parts by weight of a 40% solution of zinc bis (isobutylmaleate) catalyst to 100 parts by weight of Polyisocyanate composition 2A at a temperature of 84° C. and under a nitrogen blanket. The reaction mixture was stirred for three hours. Thereafter the catalyst was killed with benzoylchloride in a molar ratio of 1:1.2 and the temperature cooled down.

Another polyisocyanate composition (referred to hereinafter as Polyisocyanate 2C) was prepared by the addition under intense stirring of 1 part by weight of Fluowed EA 800 and 1 part by weight of L-4528 (formula $C_8F_{17}SO_2N(CH_3)CH_2$—$CH_2OH$) to 100 parts by weight of Rubinate M at a temperature of 95° C. under a nitrogen blanket. The reaction mixture was stirred at 95° C. for another hour.

Polyisocyanate composition 2D was prepared by adding 0.06 parts by weight of a 40% solution of zinc bis(isobutylmaleate) catalyst to 100 parts by weight of Polyisocyanate composition 2C. at a temperature of 90° C. The mixture was left to stand for three hours. Thereafter the catalyst was killed with benzoylchloride in a molar ratio of 1:1.2 and the temperature cooled down.

EXAMPLE 6

Rigid polyurethane foams were prepared by standard procedures by reaction of polyols with polyisocyanates including Polyisocyanates 2A to 2D prepared according to the methods of Example 5. The formulations used for foam preparation (components expressed in parts by weight—pbw) and initial thermal conductivity (lambda) of the resultant foams are recorded in Table 3. The results indicate a further improvement in lambda when allophanate variants and/or mixed prepolymers according to the invention are used.

TABLE 3

| | | | | | | | | |
|---|---|---|---|---|---|---|---|---|
| Daltolac XR 159 | pbw | 19 | 19 | 19 | 19 | 19 | 19 | 19 |
| Daltolac XR 144 | pbw | 26 | 26 | 26 | 26 | 26 | 26 | 26 |
| Daltolac R170 | pbw | 50 | 50 | 50 | 50 | 50 | 50 | 50 |
| Daltocel F455 | pbw | 1.5 | 1.5 | 1.5 | 1.5 | 1.5 | 1.5 | 1.5 |
| Arconate 1000 | pbw | 1.5 | 1.5 | 1.5 | 1.5 | 1.5 | 1.5 | 1 |
| RS 201 | pbw | 2.5 | 2.5 | 2.5 | 2.5 | 2.5 | 2.5 | 2.5 |
| Catalyst SFC | pbw | 2.5 | 2.5 | 2.5 | 2.5 | 2.5 | 2.5 | 2.5 |
| Polycat 5 | pbw | 0.3 | 0.3 | 0.3 | 0.3 | 0.3 | 0.3 | 0.3 |
| Water | pbw | 1.4 | 1.4 | 1.4 | 1.4 | 1.4 | 1.4 | 1.4 |
| HCFC 141b | pbw | 28.9 | 28.9 | 28.9 | 28.9 | 28.9 | 28.9 | 28.9 |
| FC 75 | pbw | — | — | 4.0 | — | 4.0 | — | 4.0 |
| Rubinate M | pbw | 131.0 | — | — | — | — | — | — |
| Polyisocyanate 2A | pbw | — | 131.0 | 131.0 | — | — | — | — |
| Polyisocyanate 2B | pbw | — | — | — | 131.0 | 131.0 | — | — |
| Polyisocyanate 2D | pbw | — | — | — | — | — | 131.0 | 131.0 |
| Lambda initial | mW/m°K | 18.4 | 18.3 | 17.8 | 17.9 | 17.4 | 17.5 | 17.2 |

EXAMPLE 7

A polyisocyanate composition was prepared according to the method described in Example 3 starting from 100 parts by weight of Suprasec X2185 (available from Imperial Chemical Industries) and 0.4 parts by weight of Fluorad FC10. This polyisocyanate composition is referred to hereinafter as Polyisocyanate 3A.

EXAMPLE 8

Rigid polyurethane foams having open cells were prepared according to the method described in European patent application No. 0498628. The formulations used for foam preparation (components expressed in parts by weight—pbw) and various properties of the resultant foams are recorded in Table 4. The results indicate a significant reduction in cell size using a polyisocyanate composition according to the present invention and an even greater reduction when this process is carried out in the presence of a urethane-modified isocyanate ended prepolymer as described in European patent application no. 543536. This latter process also enables to reduce the level of fluorinated additive without impairing cell size properties.

TABLE 4

| Polyol Component | | | | | | | | |
|---|---|---|---|---|---|---|---|---|
| Polyol B | pbw | 70 | 70 | 70 | 70 | 70 | 70 | 70 |
| Polyol C | pbw | 30 | 30 | 30 | 30 | 30 | 30 | 30 |
| Catalyst LB | pbw | 1.8 | 1.8 | 1.8 | 1.8 | 1.8 | 1.8 | 1.8 |
| Fixapret NF | pbw | 1.8 | 1.8 | 1.8 | 1.8 | 1.8 | 1.8 | 1.8 |
| DC 193 | pbw | 4 | 4 | 4 | 4 | 4 | 4 | 4 |
| Perfluoropentane | pbw | 10 | — | — | — | — | — | — |
| Polyisocyanate component | | | | | | | | |
| Suprasec DNR | pbw | 118 | 118 | — | — | — | — | — |
| Polyisocyanate 3A | pbw | — | — | 119.3 | 79.5 | 79.5 | 79.5 | 79.5 |
| B 8407 | pbw | — | — | 0.7 | 0.5 | 0.5 | 0.5 | 0.5 |
| Suprasec 2021 | pbw | — | — | — | 20 | 20 | 20 | 20 |
| Perfluoropentane | pbw | — | 10 | 10 | 10 | 7 | 5 | 3 |
| Foam properties | | | | | | | | |
| Closed cell content | % | 0 | 0 | 0 | 0 | 0 | 0 | 0 |
| Cell size | (micron) | 120 | 130* | 50 | 20–30 | 20–30 | 20–40 | 20–40 |

*Not stable in time.

We claim:

1. Process for the preparation of a rigid polyurethane or urethane-modified polyisocyanurate foam by reaction of a polyisocyanate composition with a polyfunctional isocyanate-reactive composition under foam-forming conditions, characterized in that the polyisocyanate composition comprises the reaction product of a stoichiometric excess of an organic polyisocyanate and (a) substantially fluorinated isocyanate-reactive compound(s).

2. Process according to claim 1 wherein the substantially fluorinated isocyanate-reactive compound is a compound of formula (I):

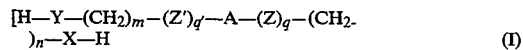

$$[H-Y-(CH_2)_m-(Z')_{q'}-A-(Z)_q-(CH_2)_n-X-H] \quad (I)$$

wherein n is an integer of from 1 to 11;
m is 1 to 11;
p is 0 or 1;
q is 0 or 1;
q' is 0 or 1;
Y is oxygen, sulphur, the group of formula

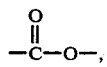

$$-\overset{O}{\underset{\|}{C}}-O-,$$

or a group of formula

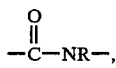

—SO$_2$—NR— or —NR—, where R is hydrogen C$_{1-12}$ alkyl, C$_{1-12}$ fluorinated alkyl;

X is oxygen, sulphur, the group of formula

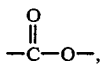

or a group of formula

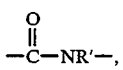

—SO$_2$—NR'— or —NR'—, where R' is C$_{1-12}$ alkyl, C$_{1-12}$ fluorinated alkyl, hydrogen or the group of formula —(CH$_2$)$_n$—(Z)$_q$—A—[(Z')$_{q'}$—(CH$_2$)$_m$—Y—H]$_p$;

Z and Z' each independently are groups of formula

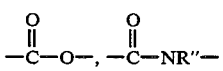

or —SO$_2$—NR'' where R'' is hydrogen, C$_{1-12}$ alkyl, C$_{1-12}$ fluorinated alkyl or the group of formula —(CH$_2$)$_n$—A—[(CH$_2$)$_m$—Y—H]$_p$ or the group of formula—R'''—Y—H where R''' is C$_{1-12}$ alkylene;

and either
  (i) when p is 0, A is substantially fluorinated or perfluorinated straight or branched chain alkyl group containing from 2 to 10 carbon atoms;
or
  (ii) when p is 1, A is substantially fluorinated or perfluorinated, straight of branched chain alkylene group containing from 2 to 10 carbon atoms.

3. Process according to claim 2 wherein the substantially fluorinated isocyanate-reactive compound is a compound of formula (I) as defined in claim 2 wherein X and Y are both oxygen.

4. Process according to claim 3 wherein the substantially fluorinated isocyanate-reactive compound is a compound of formula (II)

A—(CH$_2$)$_n$—OH        (II)

wherein A is a substantially fluorinated or perfluorinated, straight or branched chain alkyl group containing from 2 to 10 carbon atoms and n is 1 to 11.

5. Process according to claim 3 wherein the substantially fluorinated isocyanate-reactive compound is a compound of formula (III)

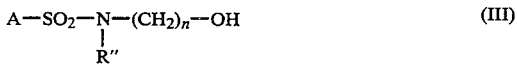

wherein A is a substantially fluorinated or perfluorinated, straight or branched chain alkyl group containing from 2 to 10 carbon atoms, n is 1 to 11 and R'' is hydrogen or a C$_{1-12}$ alkyl or —R'''—OH where R''' is C$_{1-12}$ alkylene.

6. Process according to claim 1 wherein the polyisocyanate composition is the reaction product of the organic polyisocyanate and from 0.02 to 5% by weight of the substantially fluorinated isocyanate-reactive compound(s), based on the weight of the organic polyisocyanate.

7. Process according to claim 1 wherein two or more different substantially fluorinated isocyanate-reactive compounds are used in the formation of the reaction product.

8. Process according to claim 1 wherein the polyisocyanate composition comprises the allophanate variant of said reaction product.

9. Process according to claim 1 wherein the organic polyisocyanate with which the substantially fluorinated isocyanate-reactive compound(s) is (are) reacted to form the polyisocyanate composition is diphenylmethane diisocyanate in the form of its 2,4'-, 2,2'- or 4,4'-isomer, or an oligomeric polymethylene polyphenylene polyisocyanate, or any mixture thereof.

10. Process according to claim 1 wherein said process is carried out in the presence of an inert, insoluble fluorinated compound.

11. Process according to claim 10 wherein the inert, insoluble fluorinated compound is selected from the group consisting of substantially fluorinated or perfluorinated hydrocarbons, substantially fluorinated or perfluorinated ethers, substantially fluorinated or perfluorinated tertiary amines, substantially fluorinated or perfluorinated amino-ethers and substantially fluorinated or perfluorinated sulphones.

12. Process according to claim 10 wherein the amount of inert, insoluble fluorinated compound ranges from 0.01 to 5% by weight based on the total reaction mixture.

13. Process according to claim 10 wherein the process is carried out in the presence of an isocyanate-reactive cyclic carbonate or isocyanate-reactive cyclic urea as blowing promotor and in the presence of a metal salt catalyst.

14. Rigid polyurethane or urethane-modified polyisocyanurate foam obtainable by the process of claim 1.

15. Polyisocyanate composition comprising the reaction product of a stoichiometric excess of an organic polyisocyanate and (a) substantially fluorinated isocyanate-reactive compound(s) characterized in that the organic polyisocyanate is diphenylmethane diisocyanate in the form of its 2,4'-, 2,2'- or 4,4'-isomer, or an oligomeric polymethylene polyphenylene polyisocyanate, or any mixture thereof, and the substantially fluorinated isocyanate-reactive compound is a compound of formula (I):

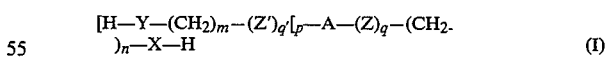

wherein n is an integer of from 1 to 11;
  m is 1 to 11;
  p is 0 or 1;
  q is 0 or 1;
  q' is 0 or 1;
  Y is oxygen, sulphur, the group of formula

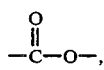

or a group of formula

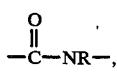

—SO$_2$—NR— or —NR—, where R is hydrogen, C$_{1-12}$ alkyl, or C$_{1-12}$ fluorinated alkyl;

X is oxygen, sulphur, the group of formula

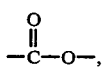

or a group of formula

—SO$_2$—NR'— or —NR'—, where R' is C$_{1-12}$ alkyl, C$_{1-12}$ fluorinated alkyl, hydrogen or the group of formula —(CH$_2$)$_n$—(Z)$_q$—A—[(Z')$_{q'}$—(CH$_2$)$_m$—Y—H]$_p$;

Z and Z' each independently are groups of formula

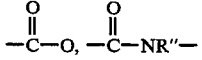

or —SO$_2$NR'' where R'' is hydrogen, C$_{1-12}$ alkyl, C$_{1-12}$ fluorinated alkyl or the group of formula —R'''—Y—H where R''' is C$_{1-12}$ alkylene;

and either (i) when p is 0, A is substantially fluorinated or perfluorinated straight or branched chain alkyl group containing from 2 to 10 carbon atoms;

or (ii) when p is 1, A is substantially fluorinated or perfluorinated, straight of branched chain alkylene group containing from 2 to 10 carbon atoms.

16. Polyisocyanate composition according to claim 15 wherein the substantially fluorinated isocyanate-reactive compound is a compound of formula (II)

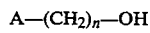 (II)

wherein A is a substantially fluorinated or perfluorinated, straight or branched chain alkyl group containing from 2 to 10 carbon atoms and n is 1 to 11.

17. Polyisocyanate composition according to claim 15 wherein the substantially fluorinated isocyanate-reactive compound is a compound of formula (III)

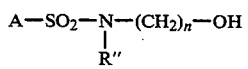 (III)

wherein A is a substantially fluorinated or perfluorinated, straight or branched chain alkyl group containing from 2 to 10 carbon atoms, n is 1 to 11 and R'' is hydrogen or a C$_{1-12}$ alkyl or —R'''—OH where R''' is C$_{1-12}$ alkylene.

18. Polyisocyanate composition according to claim 15 wherein two or more different substantially fluorinated isocyanate-reactive compounds are used to form the reaction product.

19. Polyisocyanate composition according to claim 15 containing the allophanate variant of said reaction product.

20. Polyisocyanate composition according to claim 15 wherein said composition further comprises an inert, insoluble fluorinated compound.

21. Polyisocyanate composition according to claim 20 wherein the amount of said inert, insoluble fluorinated compound ranges from 0.1 to 10% by weight based on the total polyisocyanate composition.

22. Polyisocyanate composition according to claim 20 wherein said composition further comprises a non-isocyanate-reactive surfactant.

23. Process for the preparation of a polyisocyanate composition as defined in claim 15 which comprises addition of the substantially fluorinated isocyanate-reactive compound(s) to a stoichiometric excess of the organic polyisocyanate.

* * * * *